United States Patent [19]
Collis, Jr.

[11] Patent Number: 4,827,928
[45] Date of Patent: May 9, 1989

[54] SURGICAL INSTRUMENT

[76] Inventor: John S. Collis, Jr., Brainard Pl., 29001 Cedar Rd., Cleveland, Ohio 44124

[21] Appl. No.: 150,623

[22] Filed: Feb. 1, 1988

[51] Int. Cl.$^4$ .............................................. A61F 17/32
[52] U.S. Cl. .................................. 128/305; 128/92 VJ
[58] Field of Search ............... 128/92 VJ, 92 E, 92 B, 128/304, 305, 305.1, 310, 317; 15/236 R, 303; D24/28

[56] References Cited

U.S. PATENT DOCUMENTS

| | | | |
|---|---|---|---|
| 3,716,057 | 2/1973 | Rubin | 128/305 R |
| 4,467,801 | 8/1984 | Whiteside | 128/303 R |
| 4,712,546 | 12/1987 | Noe | 128/305 |

FOREIGN PATENT DOCUMENTS 1049053  10/1983  U.S.S.R. .......................... 128/92 VJ

Primary Examiner—Robert A. Hafer
Assistant Examiner—Charles H. Sam
Attorney, Agent, or Firm—Pearne, Gordon, McCoy & Granger

[57] ABSTRACT

A surgical instrument is especially adapted for use in various surgical procedures, including use in removing disc material between vertebrae. The instrument has a handle and a flat, L-shaped working portion or body. The edges adjacent to the corners at the outer, forward end of the body are sharpened to provide the cutting edges. The instrument is placed between the vertebrae and rotated back and forth to remove disc material.

11 Claims, 1 Drawing Sheet

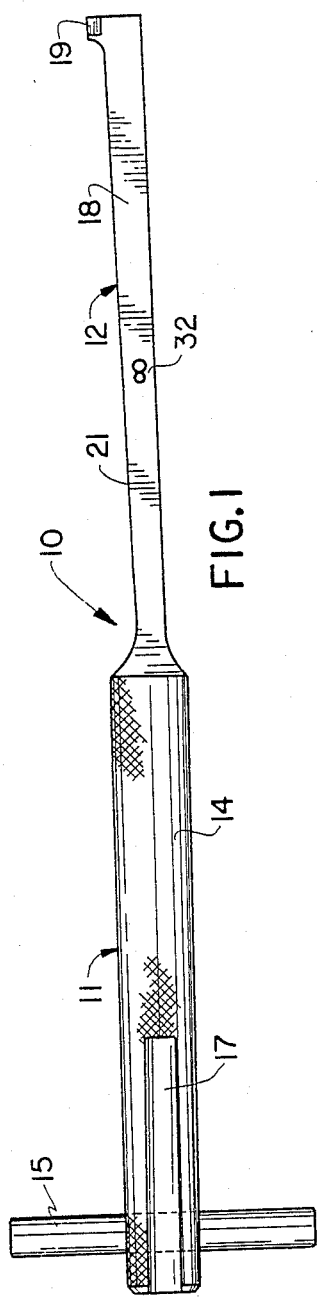
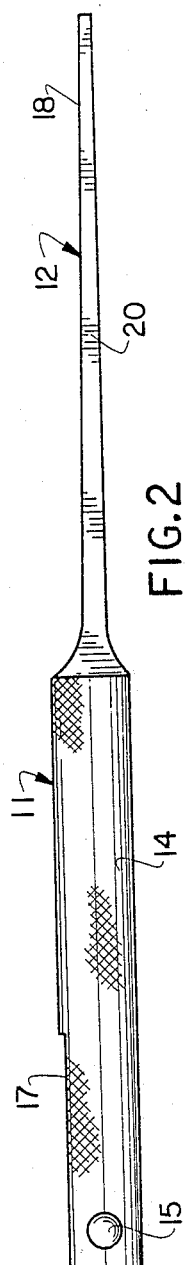
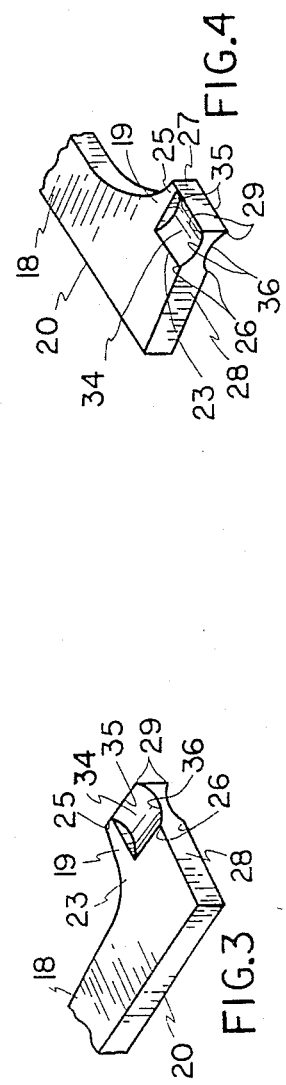

SURGICAL INSTRUMENT

BACKGROUND OF THE INVENTION

1. Field of the Invention

This invention relates to medical instruments, and more particularly to surgical instruments, such as reamers for removing bone or tissue by rotating the instrument back and forth.

2. Description of the Prior Art

A technique developed fairly recently for repairing ruptured vertebrae discs involves a replacement of the disc material with substitute bone material. As part of this technique, it is necessary to remove the disc material carefully between the vertebrae.

Prior instruments for removal of this material were inadequate because they did not permit thorough and efficient removal of the disc material. The space between the vertebrae is small and requires specialized instruments to efficiently and effectively remove the disc material. Prior art instruments were inefficient, and required that the surgery take longer than necessary.

There is a need for an instrument to perform disc removal procedures thoroughly and effectively so that the disc replacement surgery can be conducted safely, efficiently, and effectively.

U.S. Pat. No. 4,660,557, issued to the present inventor, discloses a surgical instrument specially designed for removal of the disc material between the vertebrae. This instrument has proven to be especially effective for disc replacement surgery in the lumbar region. However, the design of this instrument is not effective for surgery in the cervical region, in which the space between the vertebrae is smaller and in which it is more difficult to rotate the instrument in a full circle to remove the disc material.

There is a need for an instrument which can be specially adapted for use in the cervical region for removal of the disc material in disc replacement surgery.

SUMMARY OF THE INVENTION

The present invention provides a surgical instrument which can be used for various surgical procedures, including the removal of disc material between cervical vertebrae, which provides advantages over the prior art surgical instruments and provides the capability of performing disc replacement surgery effectively and efficiently. The instrument of the present invention has a flat, L-shaped, forward working portion with cutting edges located only adjacent to the corners on one side of the instrument. The other edges are made dull to avoid the cutting of tissue other than at the corners of the instrument. The side of the working end of the instrument opposite the cutting side is flat and parallel to the longitudinal axis to provide a pivot point for the rotation of the instrument. By rotating the instrument back and forth within the space between the vertebrae, the cutting edges at the corners on the one side of the instrument effectively cut away the desired disc material. In this manner, disc material can be removed efficiently and effectively.

The instrument of the present invention may be made in a variety of widths so that the disc can be gradually removed, using wider and wider sized instruments. For example, initially a very narrow instrument can be used and inserted between the vertebrae, and rotated back and forth to remove a first layer of disc material therebetween. Following the use of the first instrument, a wider instrument can be inserted to remove an additional layer of disc material. This procedure can be continued until all of the disc material is removed. A series of surgical instruments is thus used, a narrower instrument being used first, with progressively wider instruments being used. The width of the final instrument used depends upon the width of the space between the vertebrae where the disc material is being removed.

By placing the cutting edges only at the corners on one side of the instrument, the instrument of the present invention permits removal of additional disc material at each step with special control, so that no other matter is undesirably removed. After all of the disc material is removed, it is not necessary to employ any further instruments which would otherwise damage the vertebrae or cause problems with other tissue in the spinal area.

By providing a cutting edge only one one side of the instrument, rather than both sides of the instrument, as was done in prior art instruments, the instrument of the present invention avoids the possibility of cutting and removing delicate tissue during the removal process, since the cutting is localized on one side of the instrument. The other side of the instrument can be used as a pivot point to assist in precisely rotating the instrument.

The instrument of the present invention is also capable of other surgical uses in addition to use in removing disc material.

These and other advantages are achieved by the surgical instrument of the present invention. The surgical instrument comprises a handle and a generally L-shaped body extending from the handle. The body has a longitudinal portion extending from the handle and a tab at the forward end of the shank portion opposite the handle. The tab extends from one side of the longitudinal portion. The tab has top and bottom surfaces, each substantially flat. Each of the top and bottom surfaces has a forward edge extending the width of the instrument at the forward end opposite the handle. Each of the top and bottom surfaces also has an outer side edge along the side of the tab extending opposite the longitudinal portion. The intersection of each forward edge and each outer side edge forms a forward end corner. The tab also has an outer side surface connecting the outer side edge of the top surface and the outer side edge of the bottom surface. The tab also has a forward end surface connecting the forward edge of the top surface and the forward edge of the bottom surface. A portion of each of the forward end surfaces adjoining each of the forward end corners is sharpened to provide the cutting edges. The remaining portions of the forward edges are dulled.

BRIEF DESCRIPTION OF THE DRAWINGS

FIG. 1 is a top plan view of the instrument of the present invention;

FIG. 2 is a side elevational view of the instrument of FIG. 1;

FIG. 3 is a detailed perspective view of the forward end of the instrument of FIGS. 1 and 2; and FIG. 4 is another detailed perspective view of the forward end of the instrument of FIG. 3 taken from the other side.

DETAILED DESCRIPTION OF THE PREFERRED EMBODIMENT

Referring more particularly to the drawings, there is shown a surgical instrument 10 according to the present invention. The surgical instrument 10 comprises a cylindrical T-shaped handle 11 and a generally flat working portion or body 12 having an L-shaped forward end.

The handle 11 of the instrument comprises a shank portion 14 and a crossbar 15. The shank portion 14 is knurled to assist in gripping the instrument and includes a flat surface or key 17 extending longitudinally along the shank portion 14 from the end of the handle opposite the body 12. The key 17 assists the surgeon by providing a tactile means for determining the orientation of the flat body 12. The plane of the key 17 extends generally parallel to the plane of the flat body 12. The crossbar 15 extends through an opening in the shank portion 14 near the end of the handle opposite the body 12. The crossbar 15 extends outwardly from the handle shank portion 14 and assists the surgeon in rotating the instrument during the surgical procedure. The crossbar 15 should extend from the shank portion 14 in the direction generally parallel to the plane of the body 12. The crossbar 15 extends perpendicularly to the shank portion 14.

The body 12 comprises a longitudinal portion 18 extending from the shank portion 14 of the handle 11 and a forward head portion or tab 19 extending outwardly from one side of the longitudinal portion 18 at the forward end of the instrument, providing the body with an "L" shape. The longitudinal portion 18 of the body 12 is significantly narrower and thinner than the handle 11 at the junction between the body 12 and the handle 11. The flat longitudinal portion 18 is tapered so as to become progressively thinner toward the forward end of the instrument. The width of the longitudinal portion 18 varies, with the narrowest portion being adjacent to the handle 11 and the widest portion being at the forward end of the instrument. One side 20 of the longitudinal portion 18 extends parallel to the axis of the instrument, while the other side 21 is tapered so that it is closest to the side 20 adjacent to the handle 11 and is farthest from the side 20 at the forward end of the instrument. The flat surfaces of the longitudinal portion 18 are thus generally trapezoidal in shape.

The tab 19 extends perpendicularly to the longitudinal portion 18 from the side 21 at the forward end of the instrument. The tab 19 has identical top and bottom surfaces 23, which are generally parallel to each other. The top and bottom surfaces 23 each extend from the side 20 of the longitudinal portion 18 to an outer side edge 25 which extends along the side of the tab 19. The forward end of each of the top and bottom surfaces 23 is defined by a forward edge 26, which extends the width of the instrument at the forward end opposite the handle. The two outer side edges 25 are joined by a side surface 27 which extends generally perpendicularly to both the top and bottom surfaces 23 along the outer side of the tab 19. The two forward edges 26 are joined by a forward end surface 28 which extends perpendicularly to the top and bottom surfaces 23 and perpendicularly to the outer side surface 27.

The top and bottom surfaces 23 are thus separated at the outer side edges 25 by the outer side surface 27, and at the forward edges 26 by the forward end surface 28. The intersection of each of the top and bottom surfaces 23 with the outer side surface 27 forms the outer side edges 25, there being two such side edges. The intersection of each of the top and bottom surfaces 23 with the forward end surface 28 forms the forward edges 26, there being two such forward edges. The intersection of each of the side edges 25 with the each of the forward edges 26 forms a forward end corner 29, there being two such forward end corners.

The body 12 is generally flat in shape, with the thickness of the instrument being less than the width, as represented by the width of the tab 19 from the side 20 of the longitudinal portion 18 to the outer side surface 27 at the forward end surface 28. The width of the forward end of the body 12 will vary, depending upon the size of the instrument. It is contemplated that a series of instruments would be needed to perform the surgical procedures with the width of the body 12 varying between 3 mm and 9 mm. For example, the surgeon may start with a narrower size instrument having a width of 3 mm to remove a portion of the disc material, and progress, using instruments with greater width, until all of the disc material is removed. The thickness of the instrument at the forward end, as represented by the width of the forward end surface 28, should only be approximately 2.8 mm. Thus, with a smaller size instrument having a body width of 3 mm, the width of the instrument is approximately 1.1 times the thickness of the instrument at the forward end of the body 12. With an instrument having a width of 9 mm, the width of the instrument may be as much as 3.2 times the thickness of the instrument at the forward end of the body. Preferably, the top surface of the longitudinal portion 18 has a marking portion 32 upon which is marked an indication of the width of the particular instrument. In FIG. 1, an 8 mm instrument is represented with the mark "8" in the position 32.

The location of the cutting edges of the instrument can best be seen with reference to FIGS. 3 and 4. Adjacent to each of the two forward end corners 29 is a recess 34, the edges of which form the cutting portions of the instrument. The portion 35 of each of the outer side edges 25 bordering the recess 34 is sharper than the other portions of the side edges 25. Likewise, the portion 36 of each of the forward edges 26 bordering each recess 34 is sharpened, while the remaining portions 37 of the forward edge are less sharp. Preferably, the edges of the portions 37 are broken off to dull these edges and make them less sharp. Thus, the cutting edges of the instrument are formed along a portion 35 of each of the side edges 25 extending from each of the forward end corners 29, and cutting edges are formed along the portion 36 of each of the forward edges 26 extending from each of the forward end corners, which are sharpened, while the remaining portions 37 of the forward edges are blunted.

In using the surgical instrument 10, the surgeon inserts the narrowest instrument desired into the space between the vertebrae and rotates the instrument back and forth about its longitudinal axis, holding the instrument by the shank portion 14 of the handle 11 and using the crossbar 15 to assist in the rotation of the instrument. As the instrument is rotated back and forth in the space, the cutting edges 35 and 36 at the forward end corners 29 of the body 12 work to remove the desired bone or disc material. Since the other edges of the body 12 are not sharp, the incidental cutting of other tissue material is avoided. Since the side 20 of the body 12 of the instrument opposite the outer side edges 25 is also dull and straight, and extends parallel to the longitudinal axis of the instrument, the side 20 can be used as a pivot point for the rotation of the instrument in its use in removing the disc or bone material.

The instrument can also be used in other surgical procedures in which tissue is to be removed in a controlled manner.

While the instrument has been shown and described with respect to a particular embodiment thereof, this is for the purpose of illustration rather than limitation, and other variations and modifications of the specific embodiment herein shown and described will be apparent to those skilled in the art, all within the intended spirit and scope of the invention. Accordingly, the patent is not to be limited in scope and effect to the specific embodiment herein shown and described, nor in any other way that is inconsistent with the extent to which the progress in the art has been advanced by the invention.

What is claimed is:

1. A surgical instrument comprising:
   a handle; and
   a generally L-shaped body extending from the handle to a forward end of the instrument opposite the handle, the body having a longitudinal portion and a tab, the longitudinal portion extending from the handle to the forward end, the tab extending away from the longitudinal portion at the forward end, the tab having:
      top and bottom surfaces, each substantially flat, each of the top and bottom surfaces having a forward edge extending the width of the instrument at the forward end, each of the top and bottom surfaces also having an outer side edge along the side of the tab opposite the longitudinal portion, the intersection of each forward edge and each outer side edge forming a forward end corner;
      an outer side surface connecting the outer side edge of the top surface and the outer side edge of the bottom surface; and
      a forward end surface connecting the forward edge of the top surface and the forward edge of the bottom surface, a portion of each of the forward edges adjoining each of the forward end corners sharpened to provide cutting edges, the remaining portions of the forward edges dulled.

2. A surgical instrument as defined in claim 1, wherein the side surface of the body opposite the outer side surface extends generally parallel to the longitudinal axis of the instrument.

3. A surgical instrument as defined in claim 1, wherein the longitudinal portion of the body increases in width from the handle toward the forward edge.

4. A surgical instrument as defined in claim 1, wherein the thickness of the body decreases from the handle toward the forward edge.

5. A surgical instrument as defined in claim 1, wherein the width of the instrument at the forward end is at least 1.1 times greater than the thickness of the instrument at the forward end.

6. A surgical instrument as defined in claim 1, wherein the top and bottom surfaces are generally parallel to each other.

7. A surgical instrument as defined in claim 1, wherein the outer side surface of the tab extends generally perpendicularly to the top and bottom surfaces.

8. A surgical instrument as defined in claim 1, wherein the side surface of the body opposite the outer side surface of the tab is dulled to permit its use as a pivot point in the rotation of the instrument.

9. A surgical instrument as defined in claim 1, wherein a portion of the side edges is sharpened to provide cutting edges, the remaining portions of the side edges being left without being sharpened.

10. A surgical instrument as defined in claim 1, wherein the handle comprises a shank portion extending from the body, the crossbar extending perpendicularly to the shank portion.

11. A surgical instrument comprising:
    a handle; and
    a generally L-shaped body extending from the handle, the handle comprising a shank portion extending from the body and a crossbar extending perpendicularly to the shank portion, the body having a longitudinal portion and a tab, the longitudinal portion extending from the handle to a forward end opposite the handle, the tab extending perpendicularly from the longitudinal portion at the forward end, the side of the body opposite the tab extending generally parallel to the longitudinal axis of the instrument and being dulled to permit its use as a pivot point in the rotation of the instrument, the tab having:
       top and bottom surfaces, each substantially flat and generally parallel to each other, each of the top and bottom surfaces having a forward edge extending the width of the instrument at the forward end, each of the top and bottom surfaces also having an outer side edge along the side of the tab opposite the longitudinal portion, the intersection of each forward edge and each outer side edge forming a forward end corner;
       an outer side surface connecting the outer side edge of the top surface and the outer side edge of the bottom surface, a portion of the side edges sharpened to provide the cutting edges, the remaining portions of the side edges left without being sharpened; and
       a forward end surface connecting the forward edge of the top surface and the forward edge of the bottom surface, a portion of each of the forward edges adjoining each of the forward end corners sharpened to provide cutting edges, the remaining portions of the forward edges dulled.

* * * * *